United States Patent [19]

Crozier

[11] 4,454,051

[45] Jun. 12, 1984

[54] ALKYL XANTHOGEN FORMATE MIXTURE AS FLOTATION AGENT

[76] Inventor: Ronald D. G. Crozier, 4 Daisy La., Ridgefield, Conn. 06877

[21] Appl. No.: 270,362

[22] Filed: Jun. 4, 1981

[51] Int. Cl.$^3$ .......................... B03D 1/02; C22B 3/00; C07C 154/02

[52] U.S. Cl. ..................................... 252/61; 266/168; 260/455 B

[58] Field of Search .................... 260/455 B; 266/168; 75/10 R, 2; 252/61

[56] References Cited

PUBLICATIONS

Reid, Organic Chemistry of Bivalent Sulfur, Chem. Publishing Co., Inc., 1962, New York, p. 149.

Primary Examiner—Henry R. Jiles
Assistant Examiner—Robert C. Whittenbaugh
Attorney, Agent, or Firm—James J. Burke, II

[57] ABSTRACT

A batch process including a circulating reactor and an agitated reactor for the production of dialkyl xanthogen formates, including means to increase yields of products, inhibiting chloroformate hydrolysis, suppress production of xanthic anhydride as a byproduct, and generally control product/byproduct yields based on intended use. Certain product mixtures are particularly useful as flotation reagents, specifically collectors in the flotation of molybdenum-bearing copper ores, where molybdenum recovery has been increased by more than 10% without adverse effects on copper recovery.

1 Claim, 1 Drawing Figure

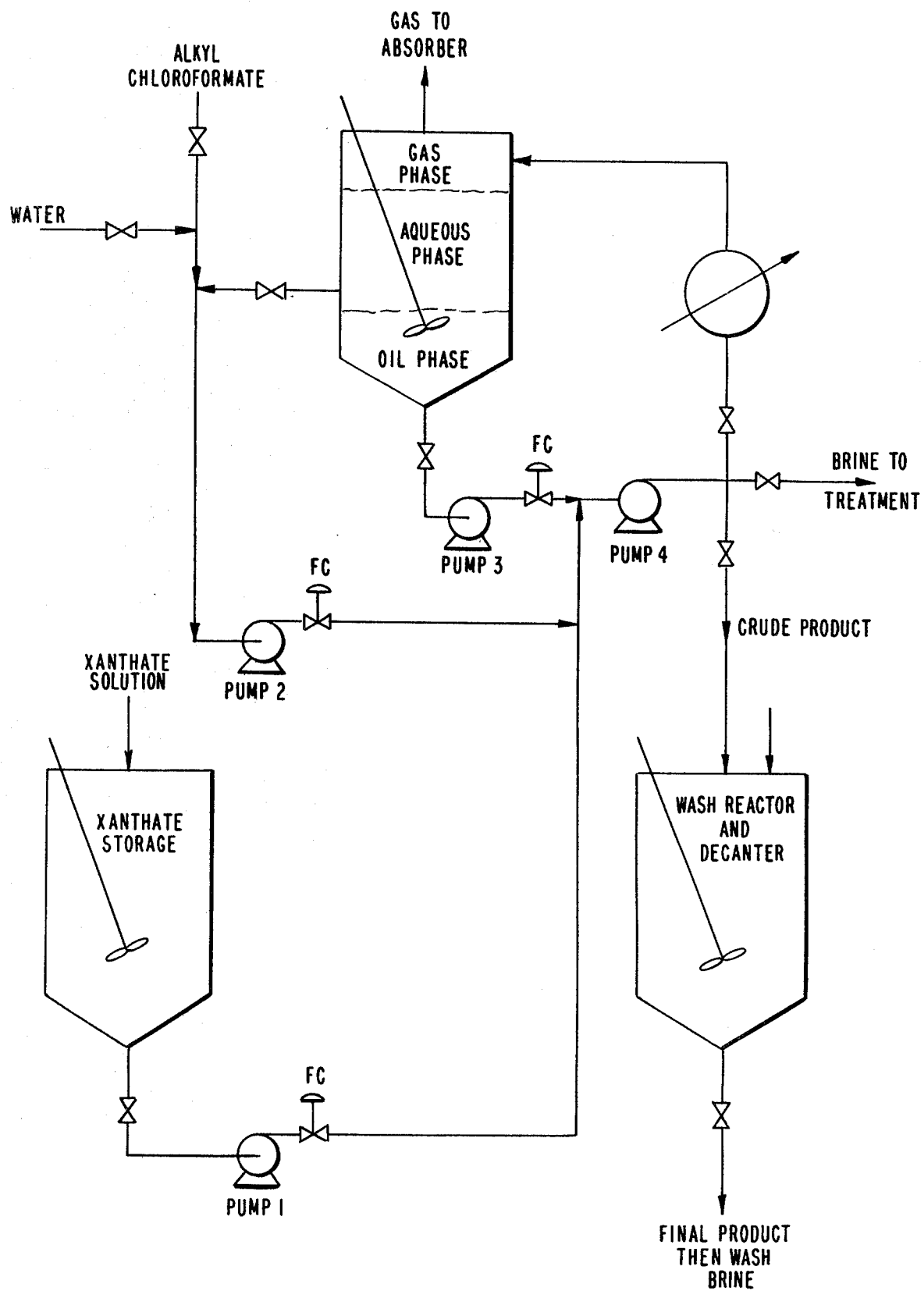

ALKYL XANTHOGEN FORMATE MIXTURE AS FLOTATION AGENT

BACKGROUND OF THE INVENTION

This invention relates to an improved industrial process for the manufacture of dialkyl xanthogen formates with the general formula:

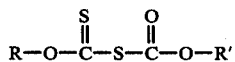

where R and R' are alkyl groups that can be identical or different, straight chain or branched, and that contain from 1 to 6 carbon atoms. The hydrogen groups may also be replaced by halogen atoms, cyanide groups or other nitrogen compounds. Unsaturated groups have also been shown to be useful in mineral reagents, pesticides and as accelerators.

These compounds have been described as useful collectors in a number of expired patents, but there are no process patents and only laboratory preparations are described in the literature. The main patents on the subject and the examples on synthesis of these products are U.S. Pat. Nos.:

Douglass 1,652,099 (1927),
Fischer 1,684,536 (1928),
Fischer 2,608,572 (1952) and
Twiss et al, (U.K. Pat. No.) 353,871 (1931).

Generally, these patents disclose laboratory procedures for preparation of compounds of this general type, but do not comment on yields or byproduct formation.

The patents cited give examples of the preparation of xanthogen formates according to the reaction:

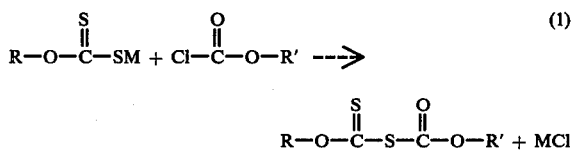

However, industrial processes have not been published or described.

The few articles on the reactions of alkali metal alkyl xanthates with alkyl chloroformates report that there are various competitive reactions which result in a reaction product which can contain impurities that are inert in the flotation process. These reactions consume a considerable proportion of the expensive starting materials, such as the alkyl chloroformates, increasing production costs.

The main articles published that describe these reactions are:

J. Welde, *Journ.f.prakt. Chemie.*, (2) Band 15, p. 44 (1887)
R. Holmberg, *Journ.f.prakt. Chemie.*, (2) Band 71, p. 264 (1905)
A. Cambron, *Canadian Journal of Research*, 2, p. 341 (1930)
R. Sayre, *J.Am. Chem. Soc.*, 74, p. 3647 (1952)
R. Felumb, *Bull. Soc. Chim. France*, p. 890 (1957)
S. M. Gurvich et al, *Zh. Prikl. Khim*, 39, (2) p. 531 (1966)

From these, different reaction conditions for reaction (1) result in a reaction product containing:

| | | | |
|---|---|---|---|
| (I) | Dialkyl xanthogen formate | $R-O-\overset{S}{\underset{\|}{C}}-S-\overset{O}{\underset{\|}{C}}-O-R'$ | 0 to 80% |
| (II) | Dialkyl xanthic anhydride | $R-O-\overset{S}{\underset{\|}{C}}-S-\overset{S}{\underset{\|}{C}}-O-R$ | 10 to 100% |
| (III) | Dialkoxy carbonyl sulfide | $R'O-\overset{O}{\underset{\|}{C}}-S-\overset{O}{\underset{\|}{C}}-O-R'$ | 0 to 40% |
| (IV) | Dialkyl carbonate | $R-O-\overset{O}{\underset{\|}{C}}-O-R'$ | 0 to 20% |
| Unreacted raw materials and other impurities | | | 0 to 10% |

The reaction mechanisms that result in this product mix have been studied by Cambron, *Op. cit.* and S. M. Gurvich et al, *Op. cit.*, and in work leading to the present invention.

Welde found that the uncontrolled reaction between potassium ethyl xanthate and ethyl chloroformate in water resulted in the production of only xanthic anhydride (II) and diethyl carbonate (IV). Holmberg used ice to cool the reaction and obtained a mixture of compounds (I) and (II), observing that a xanthate excess resulted in an increase in production of xanthic anhydride (II). Gurvich et al studied the reaction between potassium butyl xanthate and methyl chloroformate and found that COS was evolved and that the reaction product analysis varied as a function of the reaction conditions, yielding:

Compound (I): 60 to 100%
Compound (II): 0 to 30%
Compound (III): 0 to 8%

To explain this composition range they postulated the following reactions:

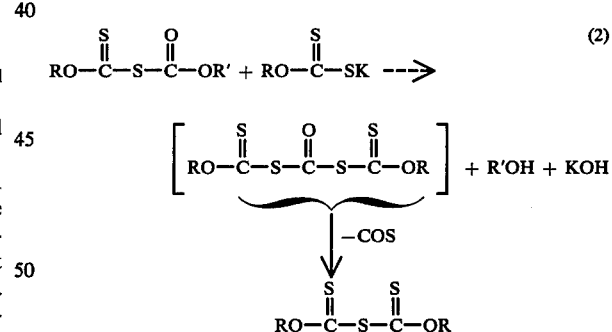

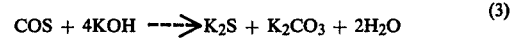

They postulate that the intermediate reaction product of reaction (2) is unstable and loses COS to form the xanthic anhydride.

The mechanism proposed by Gurvich implies that the xanthate anion attacks the C=O group of the xanthogen-formate, but this group is less active than the C=S group. Further, reaction (4) is unlikely, as if it is done independently in the laboratory yields do not reach 30%. Based on this and the work reported by Cambron and current work, the more probable reaction mechanism is:

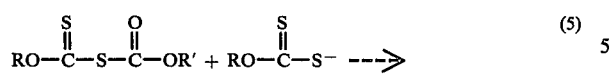

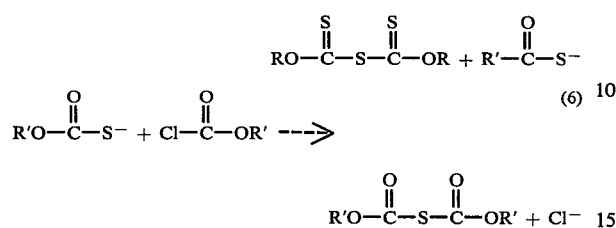

The production of compound (IV), COS and other impurities can be accounted for, in the presence of water, which is normally added to the reaction or produced in the systhesis of the xanthate, by the following reactions:

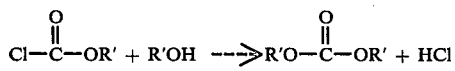

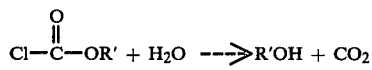

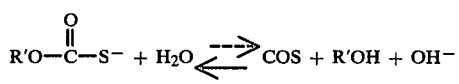

Several workers have found that high reaction temperatures favoured the production of compound (IV), which is not surprising as reaction (7) is the recommended synthesis for diethyl carbonate when carried out at 80° C. Holmberg's observation that adding the chloroformate to the xanthate favoured the production of xanthic anhydride can be deduced from reactions (2) and (5).

Cambron (p. 346) describes an experiment which supports reaction (2) when xanthate is added to a xanthogen formate.

OBJECTS OF THE INVENTION

The objects of this invention are an improved industrial process for the manufacture of dialkyl xanthogen formates based on the reaction of an aquous solution of an alkali metal alkyl xanthate with an alkyl chloroformate which:

Increases the yield of the final product;

Provides a method of controlling side reactions to give a predictable final composition and thus optimize the metallurgical and physical properties of the froth flotation collectors produced;

Provides a method of controlling the freezing point of the collector independently of the collector composition; and Provides an equipment design which is capable of producing dialkyl xanthogen formates in which either alkyl group may have from 1 to 6 carbon atoms, the alkyl groups can be branched or straight chained, saturated or unsaturated, and where hydrogens can be substituted with more polar groups such as halogens, cyanides or other nitrogen groups.

Various other objects and advantages of the invention will become clear from the following description of embodiments, and the novel features will be particularly pointed out in connection with the appended claims.

THE DRAWING

Reference will hereinafter be made to the accompanying drawing, which is a simplified schematic flow sheet or flow diagram illustrating an embodiment of the invention.

DESCRIPTION OF EMBODIMENTS

The essential element of maintaining control over the reaction between a chloroformate and a xanthate is to provide means of restricting the reaction to a zone where the relative proportions of the two reacting phases is fixed and relatively constant, and where there is good control over the reaction temperature. A continuous process is economically un-attractive because the alkyl chloroformate is very soluble in the xanthogen formate, as well as being highly corrosive, so that if the reaction is carried out with a considerable excess of chloroformate, which minimizes xanthic anhydride production, the end product would have to be distilled to remove unreacted chloroformate. As the xanthogen formate is thermally unstable, this distillation necessarily would have to be a vacuum operation. A batch reaction has a continuosly variable ratio of xanthate to chloroformate, which means that the only way to control the xanthic anhydride content in the final product is by maintaining a very low reaction temperature, which reduces the reaction rate and requires long cycles and large reactors with large energy consumption in agitation. The process of the invention simulates a continuous reactor by employing a pump/heat exchanger combination recirculating the different phases from a storage reactor and combining them with fresh xanthate solution, which then reacts in a heat exchanger at a controlled temperature. The reaction is then finished by starting up an agitator in the storage reactor. The flow sheet is shown in the drawing.

The process consists of a unit where an aqueous or alcoholic solution of alkali metal alkyl xanthate is stored and metered to a xanthogen formate reactor. The xanthogen formate storage reactor is first loaded with water into which an alkyl chloroformate is metered and agitated until an emulsion is formed and recirculated through the heat-exchanger. To this recirculation stream, a metered amount of xanthate solution is fed and the reaction temperature is adjusted according to the alkyl groups involved. During the reaction, the chloroformate partitions between the water and oily phase, requiring that these two phases be metered independently to the heat exchanger, where the main reaction is occurring. When the xanthate solution has all been fed to the xanthogen formate reaction, the agitation is started to complete the reaction. When the temperature stops rising or the temperature controller calls for no more cooling, the agitation is shut off, and the phases are allowed to decant. Normally the lower phase is the oily product. This is transferred to the wash reactor where remaining alkali metal chloride and un-reacted xanthate are removed by washing with water. The phases are separated by decantation and the oily phase stored. The water phase is normally discarded. The brine phase in the xanthogen formate reactor, which contains most of the alkali metal chloride produced in the reaction, is sent for treatment prior to discard. If the xanthate employed was in an alcoholic solution, the alcohol is recovered by distillation.

Xanthate is prepared using known methods. For alcohols which contain more than 2 carbon atoms, the xanthate reaction is performed normally in an inert organic media, such as toluene, benzene, hexane etc. Normally, the xanthate is made employing a 10 to 30% excess of alcohol and a 3 to 5% excess of caustic soda referred to carbon disulfide. This ensures that no unreacted $CS_2$ remains in the xanthate which could be deleterious if contained in the final xanthogen formate. The alcohol is added to the inert media and powdered, pellet or flake caustic added to the reactor to form the alcoholate. This reaction is highly exothermic and will require refluxing and strong cooling. The $CS_2$ is added slowly to the alcoholate maintaining the temperature at a maximum level that depends on the alkyl group involved; usually below 30° to 40° C. After the xanthate reaction is complete, the xanthate in suspension in the inert media is dissolved in water and the solution decanted and transferred to the holding tank that feeds the xanthogen formate reactor.

In the case of sodium ethyl xanthate the reaction is carried out with a 100 to 200% excess alcohol, and enough water to maintain the xanthate in solution. With this procedure 50% caustic may be employed, which is considerably cheaper than solid caustic soda.

The xanthogen formate reaction is carried out in the xanthogen formate reactor, which is first loaded with enough water so that the total water employed in the xanthate solution plus the amount added to the xanthogen formate reactor is capable of dissolving all the sodium chloride formed in the chloroformate reaction. To the water added to the reactor, or simultaneously while adding the water through the recirculation pump, a measured amount of alkyl chloroformate is added to the reactor and agitated to form an emulsion. Normally the chloroformate employed is 95 to 97% molar of the theoretical amount required to react all the xanthate that will be fed to the reactor. As the yield of xanthate is of the order of 88 to 94% the chloroformate employed in terms of the moles of $CS_2$ will be 85% to 90% of that theoretically required.

At the start of the reaction, pumps No. 2 and 4 are operated to recirculate chloroformate emulsion. The xanthate solution pump (1) is started at about 50% of the volumetric flow of the circulating loop. The temperature is controlled as a function of the alkyl groups involved, and the amount of xanthic anhydride desired in the final product. After ⅔ of the xanthate solution is consumed, the flow is reduced to ⅓ of the flow of pump No. 2 and pump No. 3 is started up to circulate the organic phase from the bottom of the reactor. After all the xanthate is transferred, the xanthogen formate agitator is started up, while maintaining recirculation, to complete the reaction. The reaction is complete when no more cooling water is required to maintain the reactor temperature. Normally agitation is maintained for 30 to 45 minutes after completion of the reaction.

After stopping agitation, the oily phase is decanted and transferred to the wash reactor. In the case of diethyl xanthogen formate, the ethyl monothiocarbonate formed by the reaction of Equation 5 can be recovered by adding more ethyl chloroformate to form diethoxy carbonyl sulfide (III) according to Equation 6. This is an oily product and is recovered by decantation and washing.

The amount of wash water employed in cleaning up the main product is adjusted to remove all the alkali metal chloride, leaving 3 to 6% unreacted alcohol in the product, which helps disperse the collector when added to the flotation circuit.

The main brine is distilled only in the case of the diethyl xanthogen formate, when considerable excess alcohol is employed in the manufacture of the xanthate. The recovered alcohol is returned to the xanthate reactor.

EXAMPLE 1

Production of Diethyl Xanthogen Formate

A batch of ethyl xanthogen ethyl formate was produced by preparing a sodium ethyl xanthate employing 3.5 moles of ethyl alcohol which was reacted with 1.05 moles of a 48% solution of NaOH. The reaction was fast and reached a temperature of 60° C. The alcoholate formed was cooled to 22° C. and 1.0 moles of $CS_2$ were added at such a rate that the reactor temperature was maintained between 25° and 35° C. by the internal cooling to assure that the temperature did not drop below 25° C., (otherwise xanthate can come out of solution).

The second reactor was loaded with 0.93 moles of ethyl chloroformate and an equal volume of water. The reactor was operated as described above, maintaining the heat exchanger outlet temperature at about 25° C. which kept the reactor temperature below 56° C.

The above procedure was repeated without employing recirculation, agitating the reactor and controlling the bulk temperature to 56° C. using a cooling jacket. The yields on raw materials and the final product composition were:

| Raw Material Consumption. | Agitated Reactor | Circulating Reactor |
|---|---|---|
| Kg/Kg of final product | | |
| Ethyl chloroformate | 0.656 | 0.615 |
| Carbon disulfide | 0.479 | 0.448 |
| Caustic soda (48%) | 0.529 | 0.495 |
| Final product composition (G.C.) | | |
| Compound (I) | 42.4 | 66.1 |
| Compound (II) | 25.0 | 19.2 |
| Compound (III) | 17.2 | 12.3 |
| Compound (IV) | 2.5 | 1.2 |
| Volatiles | 10.1 | 1.0 |

A second improvement to this process, which reduces chloroformate consumption, is to control excess alkalinity by neutralizing the xanthate with an inorganic acid. This inhibits hydrolysis of the chloroformate by reducing the reactions of Equation (6) and (7). This operation is not essential when a great excess of alcohol is employed in the manufacture of the xanthate, as the excess of alcohol neutralizes excess alkalinity.

EXAMPLE 2

Use of Acid Neutralization

A sample of sodium ethyl xanthate was made using 1.3 moles of ethyl alcohol, 1.07 moles of NaOH and 1.0 moles of $CS_2$. Half the sample was neutralized with sulfuric acid. Xanthogen formates prepared by the standard method used in the previous example had the following yields and product analyses:

| Raw Material Consumption | Un-neutralized | Neutralized |
|---|---|---|
| Kg/Kg of final product | | |
| Ethyl chloroformate | 0.672 | 0.612 |
| Carbon disulfide | 0.472 | 0.445 |
| Caustic soda | 0.551 | 0.529 |
| Final Product Composition (G.C.) | | |
| Compound (I) | 56.37 | 59.66 |
| Compound (II) | 20.80 | 16.27 |
| Compound (III) | 17.00 | 14.41 |
| Compound (IV) | 0.40 | 0.50 |
| Volatiles | 5.40 | 9.00 |

A third improvement in the process is to dissolve xanthic anhydride in the chloroformate prior to the reaction with the xanthate and thus shift the equilibrium of Equation 5 to favor xanthogen formate and suppress the formation of more xanthic anhydride, thus increasing yields on chloroformate.

EXAMPLE 3

Addition of Xanthic Anhydride to the Xanthogen Formate Reaction

Four samples of ethyl xanthate were made using 2.5 moles of $CS_2$. These samples were reacted with 0.95 moles of ethyl chloroformate containing 0, 6, 12 and 18% molar of diethyl xanthic anhydride. Analysis of the final product gave the following composition by Gas Chromatography:

| % Xanthic anhydride in Chloroformate | % Each compound in final product | | | | |
|---|---|---|---|---|---|
| | (I) | (II) | (III) | (IV) | Volatiles |
| 0% | 66.8 | 15.2 | 13.2 | 1.2 | 3.6 |
| 6% | 64.4 | 20.5 | 11.7 | 1.1 | 2.5 |
| 12% | 59.7 | 24.2 | 11.7 | 0.9 | 3.5 |
| 18% | 60.1 | 27.2 | 10.2 | 0.8 | 1.7 |

Normalized for the initial xanthic anhydride in the ECF the assays were:

| | | | | | |
|---|---|---|---|---|---|
| 0% | 66.8 | 15.2 | 13.2 | 1.2 | 3.6 |
| 6% | 68.5 | 15.4 | 12.4 | 1.2 | 2.5 |
| 12% | 67.8 | 13.9 | 13.3 | 1.0 | 4.0 |
| 18% | 73.3 | 11.2 | 12.4 | 1.0 | 2.1 |

EXAMPLE 4

Effect of Composition on Metallurgical Activity

A porphyry mineral, low in clays and with normal oxide content, easily floatable, whose total copper content was 1.48% with 0.013% molybdenum, was floated at 19° C. and at a pH of 4.0 for 7 minutes with the standard collector composition in use at the mine, which corresponded to 60% collector, 30% regular gasoline and 10% MIBC (methyl isobutyl carbinol). Feed to the flotation cells was:

| Collector Mix | 80 grams/ton of mineral |
|---|---|
| Frother, Dowfroth 1012 | 40 grams/ton of mineral |
| Fuel Oil | 20 grams/ton of mineral |
| Sulfuric acid | 2000 grams/ton of mineral |

The collector composition was:

| Test | Collector Composition % | | | | | |
|---|---|---|---|---|---|---|
| | 1 | 2 | 3 | 4 | 5 | 6 |
| Diethyl xanthogen formate | 70.1 | 100 | 51.2 | 51.2 | 60 | — |
| Isobutyl xanthogen ethyl formate | — | — | 13.7 | 13.7 | — | — |
| Diethyl xanthic anhydride | 12.0 | — | 15.0 | — | — | — |
| Diethyl xanthic emulsified | — | — | — | 15.0 | — | — |
| Diethoxy carbonyl sulfide | 8.4 | — | 8.9 | 8.9 | 40 | 100 |
| Inerts | 9.1 | — | 11.2 | 11.2 | — | — |

The product used in trial #1 was the standard product employed at the mine. Flotation results were as follows:

| Test | Concentrate | | | Tails | | | | |
|---|---|---|---|---|---|---|---|---|
| | WT gm | % CuT | % MoT | WT gm | % CuT | % MoT | % CuT | % MoT |
| 1 | 101.0 | 12.77 | 0.106 | 890.0 | 0.21 | 0.0024 | 87.3 | 83 |
| 2 | 87.3 | 14.89 | 0.122 | 914.0 | 0.20 | 0.0025 | 87.7 | 82 |
| 3 | 89.6 | 14.36 | 0.117 | 908.0 | 0.21 | 0.0027 | 87.1 | 81 |
| 4 | 87.0 | 14.76 | 0.140 | 909.0 | 0.21 | 0.0008 | 87.1 | 94 |
| 5 | 90.0 | 14.37 | 0.135 | 913.0 | 0.20 | 0.0010 | 87.6 | 93 |
| 6 | 79.0 | 14.04 | 0.152 | 944.0 | 0.39 | 0.0013 | 75.1 | 91 |

As can be seen from these results, comparing runs 1, 2 and 3 with 4, 5 and 6, an increase in diethoxy carbonyl sulfide (compound III) or emulsifying the diethyl xanthic anhydride (compound II) markedly improves molybdenum recovery. In test 6, where the collector consisted of pure compound III, molybdenum recovery is comparably improved, but copper is floated weakly. This indicates that molybdenum recovery can be significantly improved by combining a xanthogen formate with an increased amount of compound III or a soluble form of dialkyl xanthic anhydride (compound II).

EXAMPLE 5

Effect of Composition on Slime-containing Minerals

In this series of laboratory flotations, a high clay content ore from the same mine as in Example 4 was employed. The ore processed had copper heads of 1.45%, of which 0.36% was non-sulfide, and a molybdenum content of 0.015%. The flotation procedure and other reagents employed were the same as in Example 4; the standard reagent employed in test 1 was identical to that in the previous example. The composition of the collectors employed were:

| Test | % Composition | | |
|---|---|---|---|
| | 1 | 2 | 3 |
| Ethyl xanthogen formate | 70.5 | 49.9 | 47.3 |
| Isobutyl xanthogen formate | — | 13.4 | 12.8 |
| Diethyl xanthic anhydride | 12.0 | 11.0 | 10.4 |
| Diethoxy carbonyl sulfide | 8.4 | 15.0 | 20.0 |
| Others | 9.1 | 10.7 | 9.5 |
| Flotation Results | | | |
| Total Copper recovery % | 85.3 | 86.8 | 87.5 |
| Total Molybdenum Recovery % | 76 | — | 83 |

In this series of tests one can see that increasing the content of compound III when floating a high slime containing ore improves both copper and molybdenum recovery.

EXAMPLE 6

Control of Collector Crystallization Temperature

In most copper mines of the world, winter ambient temperatures are very low, and, more important, flotation water temperature frequently is less than 10° C. during winter months. Thus, collector freezing point is an important factor. More important is that, in the case of xanthogen formate collector, dialkyl xanthic anhydrides, where the alkyl group is methyl, ethyl or propyl, are solids with a melting point around 50° C., in solution in base xanthogen formate. As was shown in test 4 of Example 4, maintaining the xanthic anhydride in solution significantly improves molybdenum recovery. In the case of diethyl xanthic anhydride, the temperatures at which crystals of xanthic anhydride appear, as a function of composition, are:

|  | Composition % | | | |
|---|---|---|---|---|
| Ethyl xanthogen ethyl formate | 100 | 70.5 | 62 | 52 |
| Diethyl xanthic anhydride | — | 12.0 | 20 | 30 |
| Diethoxy carbonyl sulfide | — | 8.4 | 8 | 8 |
| Inerts | — | 9.1 | 10 | 10 |
| Crystallization temperature | −36.5° C. | −7° C. | +4° C. | +14° C. |

It has been found that, without a negative effect on flotation, the xanthic anhydride can be maintained in solution if methyl alcohol is added to the alcohol employed in making the original ethyl alcohol an the reaction conditions are adjusted to produce a xanthogen formate which contains 30% diethyl xanthic anhydride, the crystallization point is reduced from +14° C. to 0° C. Up to 10% molar methanol may be added without adversely affecting flotation, but the exact compound that is acting as a solubilizer has not been determined.

Various changes in the details, steps, materials and arrangements of parts, which has been herein described and illustrated to explain the nature of the invention, may be made by those skilled in the art within the principle and scope of the invention as defined in the appended claims.

What is claimed is:

1. An improved floation collector consisting essentially of a mixture of:

(I) alkyl xanthogen formate of the general formula

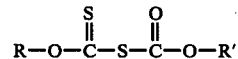

in which R and R' are selected from the group consisting of alkyl groups with 1 to 6 carbon atoms, straight chained or branched, pure or in mixtures; said formate being prepared by reaction of an alkaline alkyl xanthate and an alkyl chloroformate, and the following co-products:

 (II)

 (III)

 (IV)

wherein R and R' are defined as set forth above; and the amount of compound II in said mixture is within the range of 12 to 40%.

* * * * *